United States Patent
Vogt et al.

(10) Patent No.: US 10,675,377 B2
(45) Date of Patent: Jun. 9, 2020

(54) METHOD FOR THE PRODUCTION OF A POLYMETHYLMETHACRYLATE BONE CEMENT, BONE CEMENT KIT FOR USE IN SAID METHOD, AND BONE CEMENT PRODUCED BY SAID METHOD

(71) Applicant: Heraeus Medical GmbH, Wehrheim (DE)

(72) Inventors: Sebastian Vogt, Erfurt (DE); Thomas Kluge, Vallendar (DE)

(73) Assignee: Heraeus Medical GmbH, Wehrheim (DE)

(*) Notice: Subject to any disclaimer, the term of this patent is extended or adjusted under 35 U.S.C. 154(b) by 90 days.

(21) Appl. No.: 15/803,450

(22) Filed: Nov. 3, 2017

(65) Prior Publication Data

US 2018/0133361 A1    May 17, 2018

(30) Foreign Application Priority Data

Nov. 11, 2016 (DE) ........................ 10 2016 222 158

(51) Int. Cl.
| | |
|---|---|
| A61L 24/06 | (2006.01) |
| A61L 24/04 | (2006.01) |
| A61L 27/16 | (2006.01) |
| A61L 24/00 | (2006.01) |
| A61L 27/50 | (2006.01) |
| C08F 20/18 | (2006.01) |
| C08K 3/36 | (2006.01) |
| C08K 5/14 | (2006.01) |
| C08L 33/12 | (2006.01) |
| C08K 3/22 | (2006.01) |

(52) U.S. Cl.
CPC .......... *A61L 24/046* (2013.01); *A61L 24/001* (2013.01); *A61L 24/06* (2013.01); *A61L 27/16* (2013.01); *A61L 27/50* (2013.01); *C08F 20/18* (2013.01); *C08K 3/36* (2013.01); *C08K 5/14* (2013.01); *C08L 33/12* (2013.01); *A61L 2430/02* (2013.01); *C08K 2003/2241* (2013.01); *C08L 2203/02* (2013.01)

(58) Field of Classification Search
CPC ...................................................... A61L 24/06
See application file for complete search history.

(56) References Cited

U.S. PATENT DOCUMENTS

| | | |
|---|---|---|
| 4,671,263 A | 6/1987 | Draenert |
| 4,758,096 A | 7/1988 | Gunnarsson |
| 4,973,168 A | 11/1990 | Chan |
| 5,100,241 A | 3/1992 | Chan |
| 5,236,971 A | 8/1993 | Murray |
| 5,344,232 A | 9/1994 | Nelson et al. |
| 5,586,821 A | 12/1996 | Bonitati et al. |
| 5,588,745 A | 12/1996 | Tanaka et al. |
| 5,624,184 A | 4/1997 | Chan |
| 5,997,544 A | 12/1999 | Nies et al. |
| 6,033,105 A | 3/2000 | Barker et al. |
| 2004/0220297 A1* | 11/2004 | Bonfield ............... A61K 6/083 523/116 |
| 2011/0054392 A1* | 3/2011 | Nies .................... A61L 24/0036 604/82 |
| 2012/0035296 A1 | 2/2012 | Nakamura et al. |
| 2012/0046385 A1 | 2/2012 | Nakamura et al. |
| 2012/0302657 A1* | 11/2012 | Moszner ............. A61K 6/0094 522/24 |
| 2012/0308633 A1 | 12/2012 | Shou-Cang et al. |
| 2014/0024739 A1 | 1/2014 | Vogt |
| 2014/0135418 A1 | 5/2014 | Vogt |
| 2014/0323662 A1 | 10/2014 | Kwan et al. |

FOREIGN PATENT DOCUMENTS

| | | |
|---|---|---|
| DE | 3640279 | 6/1987 |
| DE | 102009031178 | 9/2010 |
| DE | 102014109234 | 1/2016 |
| EP | 0692229 | 1/1996 |
| EP | 1005901 | 6/2000 |
| EP | 1016452 | 7/2000 |
| EP | 1020167 | 7/2000 |

(Continued)

OTHER PUBLICATIONS

Mori, R. et al., 'Increased antibiotic release from a bone cement containing bacterial cellulose', Clinical Orthopaedics and Related Research. 2011, vol. 469, No. 2, pp. 600-606.

Franco-Marquès, E. et al., 'Thermal and dynamic mechanical characterization of acrylic bone cements modified with biodegradable polymers', Journal of Applied Polymer Science. 2013, vol. 128, No. 5, pp. 3455-3464.

(Continued)

*Primary Examiner* — Michael F Pepitone

(74) *Attorney, Agent, or Firm* — Stradley Ronon Stevens & Young, LLP

(57) ABSTRACT

A polymethylmethacrylate bone cement is produced by a method. The method comprises the steps of a) providing a cement powder comprising: at least one particulate polymethylmethacrylate or polymethylmethacrylate-copolymer wherein the at least one particulate polymethylmethacrylate or polymethylmethacrylate-copolymer have a particle size of less than 100 μm; an initiator; and at least one particulate or fibrous additive that is insoluble in methylmethacrylate, wherein the additive has an absorption capacity at room temperature of more than or equal to 0.6 g methylmethacrylate per gram of additive; b) providing a monomer solution comprising: at least one methylmethacrylate; and at least one activator; and c) mixing the cement powder and the monomer solution, characterised in that the mixing takes place without the application of shearing forces.

25 Claims, No Drawings

(56) References Cited

FOREIGN PATENT DOCUMENTS

| EP | 2402041 | 1/2012 | | |
|----|---------|--------|---|---|
| EP | 2687239 | 1/2014 | | |
| WO | 94/26403 | 11/1994 | | |
| WO | 99/67015 | 12/1999 | | |
| WO | 00/35506 | 6/2000 | | |
| WO | WO-0035506 A1 * | 6/2000 | ............ | A61L 24/06 |
| WO | 2007/025633 | 3/2007 | | |

OTHER PUBLICATIONS

OR Handbook for Simplex P Bone Cement [retrieved from the internet on Oct. 5, 2018] at https://web.archive.org/web/20151123115745/http://isulmed.com/archivos/complementos-cemento/Cemento%20Simplex%20p%20-%20Handbook%20(ingles).pdf published on Nov. 23, 2015 as per Wayback Machine.

Santos Jr. et al, "Production of Bone Cement Composites: Effect of Fillers, Co-Monomer and Particles Properties" Brazilian Journal of Chemical Engineering, vol. 28, No. 02, pp. 229-241, Apr.-Jun. 2011.

* cited by examiner

METHOD FOR THE PRODUCTION OF A POLYMETHYLMETHACRYLATE BONE CEMENT, BONE CEMENT KIT FOR USE IN SAID METHOD, AND BONE CEMENT PRODUCED BY SAID METHOD

PRIORITY

This application claims priority under 35 U.S.C. § 119(a) to DE 102016222158.2, filed on Nov. 11, 2016, the entirety of which is incorporated herein by reference.

BACKGROUND

The object of the invention is a method for the production of a polymethylmethacrylate bone cement, a bone cement kit for use in said method, and a bone cement that can be produced through said method.

Polymethylmethacrylate (PMMA) bone cements are based on the pioneering work of Sir Charnley. PMMA bone cements consist of a liquid monomer component and a powder component. The monomer component generally contains the monomer, methylmethacrylate, and an activator (N,N-dimethyl-p-toluidine) dissolved therein. The powder component, also called bone cement powder, comprises one or more polymers that are produced through polymerisation, preferably suspension polymerisation, based on methylmethacrylate and co-monomers, such as styrene, methylacrylate or similar monomers, a radiopaque agent, and the initiator, dibenzoylperoxide. Mixing the powder component and the monomer component, swelling of the polymers of the powder component in the methylmethacrylate generates a dough that can be shaped plastically and is the actual bone cement. During the mixing of powder component and monomer component, the activator, N,N-dimethyl-p-toluidine, reacts with dibenzoylperoxide while forming radicals. The radicals thus formed trigger the radical polymerisation of the methylmethacrylate. Upon advancing polymerisation of the methylmethacrylate, the viscosity of the cement dough increases until the cement dough solidifies.

Polymethylmethacrylate bone cements can be mixed through manual mixing of the cement powder and of the monomer liquid in suitable mixing beakers with the aid of spatulas. This can lead to air bubbles being enclosed in the bone cement dough, which can have a negative effect on the mechanical properties of the cured bone cement.

A large number of vacuum cementing systems has been described for preventing air inclusions in bone cement dough of which the following shall be specified here for exemplary purposes: U.S. Pat. Nos. 6,033,105 A, 5,624,184 A, 4,671,263 A, 4,973,168 A, 5,100,241 A, WO 99/67015 A1, EP 1 020 167 A2, U.S. Pat. No. 5,586,821 A, EP 1 016 452 A2, DE 36 40 279 A1, WO 94/26403 A1, EP 1 005 901 A2, and U.S. Pat. No. 5,344,232 A.

Cementing systems, in which both the cement powder and the monomer liquid are already packed in separate compartments of the mixing systems and are mixed with each other in the cementing system only right before application of the cement, are a development of cementing technology. Closed Full-Prepack mixing systems of this type have been described in patents EP 0 692 229 A1, DE 10 2009 031178 B3, U.S. Pat. No. 5,997,544 A, WO 00/35506 A1, and U.S. Pat. No. 5,588,745 A.

The use of virtually all known full-prepack mixing systems requires the medical user to manually mix the cement components, the cement powder and the monomer liquid by actuating mixing devices, such as mixing rods with stirring vanes, to form a cement dough. The homogeneity of the cement dough thus formed depends significantly on the procedure of manual mixing and can therefore be subject to variation.

Mixing methods and facilities that do not require manual mixing of the components, as are described in WO 00/35506 A1 and U.S. Pat. No. 5,588,745 A, require facilities of a complicated design and/or often work only under special prerequisites.

Accordingly, to prevent possible inhomogeneities of the cement dough, WO 00/35506 A1 proposed a storage and mixing device, in which the cement components are mixed with each other in the absence of a manually-driven mechanical mixing process. In this context, the polymethylmethacrylate bone cement powder is stored in a cartridge, whereby the cement powder takes up the entire volume of the cartridge and the volume of the intervening spaces between the particles of the cement powder is equal to the volume of the monomer liquid required for the production of bone cement dough using the cement powder stored in the cartridge. The design of this device is such that the monomer liquid is guided into the cartridge from above by the action of a vacuum and is drawn through the cement powder by a vacuum that is applied to a vacuum connector on the underside of the cartridge, whereby the air situated in the intervening spaces of the cement particles is displaced by the monomer liquid. This involves no mechanical mixing of the cement dough thus formed by means of a stirrer. It is a disadvantage of this system that the currently commercially available cement powders cannot be mixed with said device, because the rapidly swelling cement powder particles form a gel-like barrier after ingress of the monomer liquid into the cement powder to a depth of approximately 1-2 cm and impede the further migration of the monomer liquid through the entire cement powder. Moreover, conventional cement powders show a phenomenon, which is that the powder particles are wetted only poorly by methylmethacrylate due to the different surface energies. As a result, the methylmethacrylate penetrates only slowly into the cement powder.

SUMMARY OF THE INVENTION

It is therefore the object of the invention to develop a simple and non-complicated method for the mixing of polymethylmethacrylate bone cement that does not require any complicated devices, is reproducible regardless of the operating personnel, and rapidly provides a bone cement for application.

The object of the invention was therefore met through a method for the production of a polymethylmethacrylate bone cement, comprising the steps of a) providing a cement powder comprising: at least one particulate polymethylmethacrylate or polymethylmethacrylate-copolymer wherein the at least one particulate polymethylmethacrylate or polymethylmethacrylate-copolymer have a particle size of less than 100 µm; an initiator; and at least one particulate or fibrous additive that is insoluble in methylmethacrylate, wherein the additive has an absorption capacity at room temperature of more than or equal to 0.6 g methylmethacrylate per gram of additive; b) providing a monomer solution comprising: at least one methylmethacrylate; and at least one activator; and c) mixing the cement powder and the monomer solution, characterised in that the mixing takes place without the application of shearing forces.

Moreover, the object was met by a bone cement kit for use in said method. The bone cement kit comprises: a) a cement powder comprising: at least one particulate polymethylmethacrylate or polymethylmethacrylate-copolymer wherein the at least one particulate polymethylmethacrylate or polymethylmethacrylate-copolymer have a particle size of less than 100 μm; an initiator; and at least one particulate or fibrous additive that is insoluble in methylmethacrylate, wherein the additive has an absorption capacity at room temperature of more than or equal to 0.6 g methylmethacrylate per gram of additive; and b) a monomer solution comprising: at least one methylmethacrylate; and at least one activator.

The object is also met by a bone cement that is produced according to said method.

It has been found, surprisingly, that simple contacting of a cement powder defined in the following and a monomer liquid defined in the following allows a tack-free, plastically deformable bone cement dough to be produced that cures independently through radical polymerisation without there being any need to mix the cement dough manually or through the use of technical aids.

The invention is based on a surprising observation, namely that the addition of a particulate or fibrous additive that is insoluble in methylmethacrylate and has an absorption capacity at room temperature of more than 0.6 g methylmethacrylate per gram of additive to a cement powder of a low-viscosity cement allows a modified cement powder to be obtained into which monomer liquid can be pressed over a distance of at least 5 cm. The additive surprisingly also improves the wetting of the cement powder by the monomer liquid. It facilitates the ingress of the monomer liquid into the cement powder. In this context, the additive has a "wick effect". The additive guides the monomer liquid into the inside of the cement powder even in very low amounts from 0.1% by weight. Moreover, the additive delays the polymer particles from becoming sticky, whereby the formation of a blocking gel layer is delayed and the ingress of the monomer liquid into the cement powder is favoured.

Moreover, it has been evident, surprisingly, that the addition of the additive to a cement powder also allows the monomer liquid to be aspirated over a distance of at least 3.0 cm starting from the inlet point of the monomer liquid in a device according to WO 00/35506 A1 through the action of a vacuum. It has also been evident that pressing the monomer liquid into the cement powder according to the invention produces a homogeneous cement dough such that mechanical mixing of the cement components is not required. After the cement powder and the monomer liquid are mixed, this immediately generates a tack-free, plastically deformable cement dough that can be processed and applied and cures independently through radical polymerisation.

DETAILED DESCRIPTION

According to the invention, a method is provided, in which cement powder and monomer liquid are being mixed through the monomer liquid penetrating into the cement powder and/or being absorbed by the cement powder. As a result, no mechanical mixing is required, neither manually nor through technical aids, and the mixing can take place without the application of shearing forces.

Preferably, the monomer liquid and cement powder are arranged appropriately before and during the absorption such that the monomer liquid is arranged below the cement powder relative to the surface of the earth. This allows enclosed air in the cement powder to escape easily.

The terms, "contain" and "comprise", as used in the present invention shall also include the meanings "to consist of" and "essentially consist of".

Room temperature shall be understood according to the invention to be a temperature of 23° C.

The monomer liquid comprises methylmethacrylate as monomer.

Suitable polymers in the cement powder include polymethylmethacrylate and copolymers of methylmethacrylate and one or more monomers that can be copolymerised with it, such as methylacrylate, styrene, and ethylacrylate, which are present as powders.

The polymer powder is a polymer powder of the sieved fraction <100 μm. As a result, the polymer exclusively contains particles that drop through a sieve with a mesh width of 100 μm.

The invention can provide the intervening spaces in the cement powder to account for between 25% by volume and 40% by volume.

The weight fraction of the polymer of the sieved fraction <100 μm can vary widely, whereby the weight fraction in the cement powder preferably is in the range of 69.5-99.3.

The cement powder also contains a polymerisation initiator. The polymerisation initiator preferably is an activatable polymerisation initiator, e.g. a peroxide.

Peroxides are preferred. The peroxide preferably comprises no free acidic groups. The peroxide can be an organic peroxide or an inorganic peroxide, such as, for example, dialkylperoxides or hydroperoxides. For example, the peroxide can be selected from the group consisting of dibenzoylperoxide, cumene-hydroperoxide, 1,1,3,3-tetramethylbutylperoxide, t-butylperoxide, t-amyl-hydroperoxide, di-isopropylbenzen-mono-hydroperoxide, and a mixture of at least two thereof. According to a particularly preferred embodiment, the peroxide is selected from the group consisting of dibenzoyl peroxide and dilauroyl peroxide. Waterphlegmatised dibenzoylperoxide with a water content of less than 30% by weight is particularly preferred, preferably less than 28% by weight.

A fraction of 0.4-3.0% by weight, relative to the cement powder, of the initiator is added to the cement powder.

The cement powder also contains a methylmethacrylate-insoluble particulate or fibrous additive, whereby the additive has an absorption capacity at room temperature of more than or equal to 0.6 g methylmethacrylate per gram of the additive.

For determination of the absorption capacity of the additives, the Enslin apparatus known from pharmacy (C.-D. Herzfeldt, J. Kreuter (ed.): Grundlagen der Arzneiformenlehre. Galenik 2, Springer Verlag Berlin Heidelberg New York, 1999, p. 79-80.) was simplified. A glass filter crucible 1D3 from Schott was used. The tare mass of the glass filter crucible was determined first. Then 3.000 g or 1.000 g of additive was weighed into the glass filter crucible. The glass filter crucible was placed on a filter flask. 20 ml methylmethacrylate were added to the additive such that the additive was fully covered. The methylmethacrylate that was not absorbed by the additive seeped in downward direction through the glass filter crucible. After 15 minutes, the glass filter crucible with the additive and the absorbed methylmethacrylate was weighed and the mass of the absorbed methylmethacrylate was determined. The determination was repeated in triplicate and the mean was determined. As a reference, the glass filter crucible was treated in like manner with methylmethacrylate without added additive.

It is advantageous for the additive to process covalently bound hydroxyl groups on its surface. Si—OH groups and alcoholic OH groups are particularly advantageous in this context. Due to the OH groups being arranged on the surface, the additive has a high surface energy, which provides for good wettability of the additive by methylmethacrylate.

According to the invention, microcrystalline cellulose, cellulose, oxycellulose, starch, titanium dioxide, and silicon dioxide are preferred as additive. In addition, sugar alcohols, such as sorbitol, mannitol, dianhydroglucitol, and xylitol are also conceivable as additives.

In one embodiment, pyrogenic silicon dioxide is particularly preferred as additive. The pyrogenic silicic acids, Aerosil® 380 and Aerosil® 300, are particularly well-suited. Besides, it is also feasible to use silicon dioxide generated by sol-gel processes as additive.

Preferably, the additive has a particle size according to the sieved fraction of less than 100 μm, preferably according to the sieved fraction of less than 50 μm, and particularly preferably according to the sieved fraction of less than 10 μm.

At least one radiopaque agent can be admixed to the bone cement powder. The radiopaque agent can be a commonly known radiopaque agent in this field, preferably in particulate form. Suitable radiopaquer agents can be soluble or insoluble in the monomer for radical polymerisation. The radiopaque agent is preferably selected from the group consisting of metal oxides (such as, for example, zirconium oxide), barium sulfate, toxicologically acceptable heavy metal particles (such as, for example, tantalum), ferrite, magnetite (supramagnetic magnetite also, if applicable), and biocompatible calcium salts, such as calcium carbonate and calcium sulfate. In this context, zirconium dioxide, barium sulfate, calcium carbonate, and calcium sulfate are preferred. Said radiopaquer agents preferably have a mean particle diameter in the range of 10 nm to 500 μm. The concentration of admixed radiopaque agent, in particular the zirconium dioxide concentration, in the bone cement powder is preferably in the range of 0 to 30% by weight, particularly preferably in the range of 0 to 15.0% by weight.

Pharmaceutical agents, such as antiphlogistics, bisphosphonates, growth factors and, preferably, anti-infective agents and/or antiseptic agents, can be stored relatively readily over an extended period of time in the dry cement powder. Specifically, gentamicin, tobramycin, clindamycin, vancomycin, fosfomycin, colistin, and daptomycin, which can be used in the form of easily water-soluble salts or also in the form of poorly water-soluble salts or complexes, are preferred as anti-infective agents. Octenidine, dequalinium chloride, polyhexanide, calcium peroxide, and benzalkonium chloride are preferred as antiseptic agents.

The monomer liquid contains an activator. Activators from the group of aromatic amines are preferred. N,N-Dimethyl-p-toluidine, N,N-di-methyl-o-toluidine, N,N-dimethyl-aniline, N,N-bis-hydroxyethyl-p-toluidine are particularly preferred as activators.

The monomer liquid preferably also contains a radical stabiliser from the group of the quinones or sterically hindered phenols. p-Hydroquinone, o-hydroquinone, 2,6-di-t-butyl-p-hydroquinone, 2-t-butyl-p-hydrochinone, and 2,6-di-t-butyl-4-methyl-phenol are preferred as radical stabiliser.

The monomer liquid can further contain a colourant substance. The colourant is, e.g., colour pigments, food dyes or coloured lacquers. Pertinent examples include E101, E104, E132, E141 (chlorophyllin), E142, riboflavin, lissamine green, and "Farblack Gran", which is the aluminium salt of a mixture of E104 and E132. Chlorophyllin E141 is preferred.

Preferably, a fraction of 1.0 to 10% by weight of the anti-infective agents and antiseptic agents is contained in the cement powder.

In a first embodiment, the cement powder is composed of 0.0-15.0% by weight radiopaque agent, 0.4-3.0% by weight dibenzoyl peroxide, 79.5-99.3% by weight polymethylmethacrylate and/or polymethylmethacrylate-copolymer, 0.1-2.5% by weight additive.

In a second embodiment, the cement powder is composed of 1.0-10% by weight of an anti-infected agent or antiseptic agent, 0.0-15.0% by weight radiopaque agent, 0.4-3.0% by weight dibenzoyl peroxide, 69.5-98.3% by weight polymethylmethacrylate and/or polymethylmethacrylate-copolymer, 0.1-2.5% by weight additive.

The invention also comprises a polymethylmethacrylate bone cement kit. Said kit contains the cement powder described above and the monomer liquid described above, the methyl methacrylate, and at least one activator as described above.

Cement powder and monomer liquid are separate components and can be stored separately in their non-cured condition.

The polymethylmethacrylate bone cement according to the invention is intended for use in Prepac cementing systems for mechanical fixation of articular endoprostheses.

The invention is illustrated in more detail through the examples presented in the following, though without limiting the scope of the invention.

EXAMPLES

Example 1

Determination of the Absorption Capacity of the Additive

The following starting substances were used for the determination of the absorption capacity of the additive:

Methylmethacrylate (Sigma-Aldrich)

Starch (Sigma-Aldrich, sieved fraction <100 μm)

Cellulose (Sigma-Aldrich, sieved fraction <100 μm)

Aerosil® 380 (Evonik, particle size ~7 nm)

A 1D3 glass filter crucible from Schott Mainz was used for determination of the absorption capacity of the additives, starch, cellulose and Aerosil®380. The tare mass of the glass filter crucible was determined first. Then, 3.000 g of additive and, in the case of Aerosil® 380, 1.000 g were weighed into the glass filter crucible. The glass filter crucible with the weighed additive was placed on a filter flask. 10 ml methylmethacrylate were added to the additive such that the additive was fully covered. The methylmethacrylate that was not absorbed by the additive seeped in downward direction through the glass filter crucible. After 15 minutes, the glass filter crucible with the additive and the absorbed methylmethacrylate was weighed and the mass of the absorbed methylmethacrylate was determined. The determination was repeated in triplicate and the mean was determined. As a reference, the glass filter crucible was treated in like manner with methylmethacrylate without added additive.

| Additive | Absorption capacity [g methylmethacrylate/g additive] |
|---|---|
| Starch | 0.7 |
| Cellulose | 1.8 |
| Aerosil ® 380 | 9.4 |

Example 2

Mixing of Cement Powder and Monomer Liquid

The following starting substances were used for preparation of the following cement powders 1 to 11:
Methylmethacrylate-methylacrylate-copolymer;
75% dibenzoyl peroxide (BPO, phlegmatised with 25% by weight water)
Zirconium dioxide;
Starch (Sigma-Aldrich, sieved fraction <100 μm)
Cellulose (Sigma-Aldrich, sieved fraction <100 μm)
Aerosil® 380 (Evonik, particle size ~7 nm)

The components of the cement powders were weighed into 1000 ml plastic bottles. Then, the cement powders were homogenised by mixing with a TURBULA® mixer (Willy A. Bachofen AG). The mixing time was 30 minutes.

Composition of Cement Powders 1-3

| Cement powder no. | PMMA-co-MA [g] | $ZrO_2$ [g] | 75% BPO [g] | Starch [g] |
|---|---|---|---|---|
| 1 | 32.47 | 6.00 | 0.53 | 1.00 |
| 2 | 31.47 | 6.00 | 0.53 | 2.00 |
| 3 | 30.47 | 6.00 | 0.53 | 3.00 |

Composition of Cement Powders 4-6

| Cement powder no. | PMMA-co-MA [g] | $ZrO_2$ [g] | 75% BPO [g] | Cellulose [g] |
|---|---|---|---|---|
| 4 | 32.47 | 6.00 | 0.53 | 1.00 |
| 5 | 31.47 | 6.00 | 0.53 | 2.00 |
| 6 | 30.47 | 6.00 | 0.53 | 3.00 |

Composition of Cement Powders 7-11

| Cement powder no. | PMMA-co-MA [g] | $ZrO_2$ [g] | 75% BPO [g] | Aerosil ® 380 [g] |
|---|---|---|---|---|
| 7 | 33.43 | 6.00 | 0.53 | 0.04 |
| 8 | 33.34 | 6.00 | 0.53 | 0.12 |
| 9 | 33.22 | 6.00 | 0.53 | 0.25 |
| 10 | 32.97 | 6.00 | 0.53 | 0.50 |
| 11 | 32.72 | 6.00 | 0.53 | 0.75 |

A transparent hollow cylinder-shaped plastic cartridge with an internal diameter of 35 mm was used with a gas-permeable, but cement powder particle-impermeable closure head in the following experiments. A total of 40.00 g cement powder were filled into the cartridge. Then the hollow space with the cement powder was closed by a first plunger that is impermeable for cement powder particles, but is permeable for gases and liquids, and can be shifted axially in the plastic tube. A Palacos ampoule containing 20 ml of monomer liquid was placed in the hollow space behind the first plunger. Subsequently, a second plunger that was impermeable for gases, liquids, and cement powder particles and can be shifted axially in the plastic cartridge was inserted. Then the plastic tube was positioned vertically with the closure head on top. A hand-driven mechanical extrusion device (Palamixgun) was then used to push the second plunger in the direction of the closure head. Firstly, the ampoule fractured and the monomer liquid and the splinters were pressed in the direction of the second plunger. In this context, the monomer liquid was pressed through the second plunger into the cement powder. In this context, the cement powder was completely wetted by the ascending monomer liquid over a distance of 5.8 cm. After a waiting time of a few seconds, the closure head was opened and the cement dough thus formed was pressed out.

In one variant of the experiment, a vacuum connector was attached to the closure head. A total of 40.00 g cement powder each were filled in the cartridge. The cartridge was then closed with a plunger that was permeable for gases and liquids. The cartridge was stored head down and a vacuum was applied. Then, 20 ml of monomer liquid each were placed onto the plunger that is permeable for gases and liquids, and a vacuum was applied. In all cements, the monomer liquid was aspirated through the cement powder over a distance of approximately 4.0 cm.

Example 3

Test in Accordance with ISO 5833

The following starting substances were used for preparation of the following cement powders:
Methylmethacrylate-methylacrylate-copolymer;
75% dibenzoyl peroxide (BPO, phlegmatised with 25% by weight water)
Zirconium dioxide;
Gentamicin sulfate;
Clindamycin hydrochloride;
Vancomycin hydrochloride;
Daptomycin;
Trometamol-fosfomycin;
Octenidine dihydrochloride
Starch (Sigma-Aldrich, sieved fraction <100 μm)
Cellulose (Sigma-Aldrich, sieved fraction <100 μm)
Aerosil® 380 (Evonik, particle size ~7 nm)

The PMMA bone cement, PALACOS® LV+G (batch 7732, exp. 2017-06), was used as reference material.

The components of the cement powders were weighed into 1000 ml plastic bottles. Then, the cement powders were homogenised by mixing with a TURBULA mixer (Willy A. Bachofen AG). The mixing time was 30 minutes.

Composition of Cement Powders 12-14

| Cement powder no. | PMMA-co-MA [g] | $ZrO_2$ [g] | 75% BPO [g] | Starch [g] |
|---|---|---|---|---|
| 12 | 32.47 | 6.00 | 0.53 | 1.00 |
| 13 | 31.47 | 6.00 | 0.53 | 2.00 |
| 14 | 30.47 | 6.00 | 0.53 | 3.00 |

Composition of Cement Powders 15-17

| Cement powder no. | PMMA-co-MA [g] | $ZrO_2$ [g] | 75% BPO [g] | Cellulose [g] |
|---|---|---|---|---|
| 15 | 32.47 | 6.00 | 0.53 | 1.00 |
| 16 | 31.47 | 6.00 | 0.53 | 2.00 |
| 17 | 30.47 | 6.00 | 0.53 | 3.00 |

Composition of Cement Powders 18-22

| Cement powder no. | PMMA-co-MA [g] | ZrO$_2$ [g] | 75% BPO [g] | Aerosil ® 380 [g] |
|---|---|---|---|---|
| 18 | 33.43 | 6.00 | 0.53 | 0.04 |
| 19 | 33.34 | 6.00 | 0.53 | 0.12 |
| 20 | 33.22 | 6.00 | 0.53 | 0.25 |
| 21 | 32.97 | 6.00 | 0.53 | 0.50 |
| 22 | 32.72 | 6.00 | 0.53 | 0.75 |

Composition of Cement Powders 23-28

| Cement powder no. | Agent | PMMA-co-MA [g] | ZrO$_2$ [g] | 75% BPO [g] | Aerosil ® 380 [g] |
|---|---|---|---|---|---|
| 23 | 1.00 g gentamicin sulfate | 33.22 | 6.00 | 0.53 | 0.25 |
| 24 | 1.00 g clindamycin hydrochloride | 33.22 | 6.00 | 0.53 | 0.25 |
| 25 | 1.00 g vancomycin hydrochloride | 33.22 | 6.00 | 0.53 | 0.25 |
| 26 | 1.00 g daptomycin | 33.22 | 6.00 | 0.53 | 0.25 |
| 27 | 1.00 g trometamol-fosfomycin | 33.22 | 6.00 | 0.53 | 0.25 |
| 28 | 1.00 g octenidine hydrochloride | 33.22 | 6.00 | 0.53 | 0.25 |

For preparation of the cement dough and production of the test bodies, 10 ml PALA-COS® monomer liquid ampoules (batch 5276, exp. 2010-10) from Heraeus Medical GmbH were used. The monomer liquid of a 10 ml monomer ampoule consists of 9.20 g methylmethacrylate, 0.19 g N,N-dimethyl-p-toluidine, 10 ppm p-hydroquinone, and 0.2 mg chlorophyllin (E141).

Cement powders 12-28 and cement powder Palacos LV+G were mixed with the monomer liquid to produce cement dough samples. For this purpose, 20.0 g each of cement powders 12-22 were mixed with 10 ml of monomer liquid and 20.5 g of cement powders 23-28 were homogenised with 10 ml of monomer liquid. Each cement dough thus produced was used to produce strip-shaped test bodies with dimensions of (75 mm×10 mm×3.3 mm) for the determination of bending strength and flexural modulus and cylindrical test bodies (diameter 6 mm, height 12 mm) for the determination of the compressive strength. The test bodies were then stored for 24 hours on air at 23±1° C. Then the 4-point flexural strength, flexural modulus, and the compressive strength of the test bodies were determined using a Zwick universal testing device.

Results of the Tests of Flexural Strength, Flexural Modulus, and Compressive Strength According to ISO 5833 on Cement Samples 12-28

| Cement powder no. | 4-point flexural strength [MPa] | Flexural modulus [MPa] | Compressive strength [MPa] |
|---|---|---|---|
| 12 | 63.9 ± 1.3 | 2783 ± 87 | 93.0 ± 1.6 |
| 13 | 63.4 ± 1.1 | 2799 ± 80 | 93.7 ± 1.3 |
| 14 | 59.9 ± 1.4 | 2747 ± 103 | 91.6 ± 1.3 |
| 15 | 69.8 ± 1.3 | 2977 ± 96 | 94.4 ± 1.2 |
| 16 | 68.3 ± 2.0 | 2995 ± 135 | 94.4 ± 0.9 |
| 17 | 65.8 ± 1.1 | 2954 ± 57 | 92.5 ± 1.0 |
| 18 | 73.8 ± 1.3 | 3066 ± 59 | 95.6 ± 0.9 |
| 19 | 68.1 ± 2.6 | 2877 ± 20 | 97.7 ± 2.2 |
| 20 | 73.5 ± 1.4 | 2919 ± 78 | 93.2 ± 3.2 |
| 21 | 66.0 ± 2.8 | 2870 ± 60 | 84.5 ± 3.8 |
| 22 | 61.3 ± 3.2 | 2823 ± 3.1 | 89.3 ± 3.6 |
| 23 | 62.2 ± 1.9 | 2871 ± 129 | 94.8 ± 1.4 |
| 24 | 62.5 ± 2.5 | 2788 ± 138 | 92.6 ± 2.2 |
| 25 | 65.8 ± 3.7 | 3004 ± 55 | 94.6 ± 2.6 |
| 26 | 67.5 ± 1.4 | 2970 ± 24 | 93.6 ± 2.0 |
| 27 | 63.8 ± 2.4 | 2881 ± 75 | 91.2 ± 1.0 |
| 28 | 55.6 ± 1.4 | 2829 ± 91 | 89.8 ± 1.9 |
| Reference Palacos LV + G | 65.2 ± 1.7 | 2851 ± 93 | 91.2 0.9 |

ISO 5833 requires cured polymethylmethacrylate bone cement to comprise a flexible strength of at least >50 MPa, a flexural modulus of at least >1,800 MPa, and a compressive strength of at least >70 MPa. The results of the determination of the flexural strength, flexural modulus, and compressive strength of the cement samples produced using cement powders 12-28 show that the cement samples meet and clearly surpass the requirements of ISO 5833 with regard to the flexural strength, flexural modulus, and compressive strength.

The invention claimed is:
1. A method for the production of a polymethylmethacrylate bone cement comprising the steps of:
 a) providing a cement powder composition comprising:
  at least one particulate polymethylmethacrylate or polymethylmethacrylate-copolymer, wherein the at least one particulate polymethylmethacrylate or polymethylmethacrylate-copolymer has a particle size of less than 100 μm;
  an initiator comprising a peroxide compound; and
  at least one particulate or fibrous additive that is insoluble in methylmethacrylate, wherein the at least one particulate or fibrous additive has an absorption capacity at room temperature of more than or equal to 0.6 g methylmethacrylate per gram of the at least one particulate or fibrous additive;

b) providing a monomer liquid comprising:
    at least one methylmethacrylate monomer; and
    at least one activator comprising an aromatic amine; and
c) mixing the cement powder composition and the monomer liquid, such that the monomer liquid contacts the cement powder composition to produce a homogenous dough without mechanical mixing, wherein the cement powder composition comprises intervening spaces, wherein the intervening spaces account for between 25% by volume and 40% of the cement powder composition.

2. The method of claim 1, wherein the at least one particulate or fibrous additive comprises covalently bound hydroxyl groups on its surface.

3. The method of claim 1, wherein the at least one particulate or fibrous additive is selected from the group consisting of microcrystalline cellulose, oxycellulose, titanium dioxide, and silicon dioxide.

4. The method of claim 1, wherein the at least one particulate or fibrous additive is pyrogenic silicon dioxide.

5. The method of claim 1, wherein the at least one particulate or fibrous additive has a particle size of less than 100 μm.

6. The method of claim 5, wherein the at least one particulate or fibrous additive has a particle size of less than 50 μm.

7. The method of claim 6, wherein the at least one particulate or fibrous additive has a particle size of less than 10 μm.

8. The method of claim 1 wherein the at least one particulate polymethylmethacrylate or polymethylmethacrylate-copolymer was passed through a 100 μm mesh sieve.

9. The method of claim 1, wherein the cement powder contains the additive in an amount of 0.1 to 2.5% by weight, relative to the total weight of the cement powder.

10. A bone cement kit, wherein the kit comprises:
a) a cement powder composition comprising:
    at least one particulate polymethylmethacrylate or polymethylmethacrylate-copolymer wherein the at least one particulate polymethylmethacrylate or polymethylmethacrylate-copolymer has a particle size of less than 100 μm;
    an initiator comprising a peroxide compound; and
    at least one particulate or fibrous additive that is insoluble in methylmethacrylate, wherein the at least one particulate or fibrous additive has an absorption capacity at room temperature of more than or equal to 0.6 g methylmethacrylate per gram of the at least one particulate or fibrous additive; and
b) a monomer liquid comprising:
    at least one methylmethacrylate monomer; and
    at least one activator comprising an aromatic amine, wherein the cement powder composition comprises intervening spaces, wherein the intervening spaces account for between 25% by volume and 40% of the cement powder composition.

11. The kit of claim 10, wherein the at least one particulate or fibrous additive comprises covalently bound hydroxyl groups on its surface.

12. The kit of claim 10, wherein the at least one particulate or fibrous additive is selected from the group consisting of microcrystalline cellulose, oxycellulose, titanium dioxide, and silicon dioxide.

13. The kit of claim 10, wherein the at least one particulate or fibrous additive is pyrogenic silicon dioxide.

14. The kit of claim 10, wherein the at least one particulate or fibrous additive has a particle size of less than 100 μm.

15. The kit of claim 14, wherein the at least one particulate or fibrous additive has a particle size of less than 50 μm.

16. The kit of claim 15, wherein the at least one particulate or fibrous additive has a particle size of less than 10 μm.

17. The kit of claim 10, wherein the cement powder composition comprises the additive in an amount of 0.1 to 2.5% by weight, relative to the total weight of the cement powder.

18. The kit of claim 10, wherein the monomer liquid comprises methylmethacrylate.

19. The kit of claim 10, wherein the polymer powder composition comprises dibenzoyl peroxide as the initiator.

20. The kit of claim 10, wherein the monomer liquid further comprises at least one radical stabiliser selected from the group consisting of quinones and sterically hindered phenols.

21. The kit of claim 10, wherein the cement powder composition further comprises a particulate radiopaque agent.

22. The kit of claim 21, wherein the cement powder composition comprises:
    0.4-3.0% by weight of dibenzoylperoxide as the initiator;
    79.5-99.3% by weight of the polymethylmethacrylate and/or polymethylmethacrylate-copolymer; and
    0.1-2.5% by weight of the at least one particulate or fibrous additive.

23. The kit of claim 10, wherein the cement powder composition further comprises an anti-infective agent or antiseptic agent.

24. The kit of claim 23 wherein the cement powder composition comprises:
    1.0-10% by weight of the anti-infective agent or antiseptic agent;
    0.0-15.0% by weight of a radiopaque agent;
    0.4-3.0% by weight of dibenzoylperoxide as the initiator;
    69.5-98.3% by weight of the polymethylmethacrylate and/or polymethylmethacrylate-copolymer; and
    0.1-2.5% by weight of the at least one particulate or fibrous additive.

25. The bone cement produced by claim 1.

* * * * *